United States Patent [19]
Mukherjee et al.

[11] Patent Number: 5,935,589
[45] Date of Patent: Aug. 10, 1999

[54] STABLE COSMETIC COMPOSITIONS WITH DIFFERENT PH EMULSIONS

[75] Inventors: Surajit Mukherjee, Ridgewood; Stephan Habif, Demarest; Donald Rick, New Milford, all of N.J.

[73] Assignee: Chesebrough-Pond's USA Co., Greenwich, Conn.

[21] Appl. No.: 08/953,018

[22] Filed: Oct. 17, 1997

[51] Int. Cl.$^6$ .............. A61K 7/00; A61K 7/44; B01J 13/00
[52] U.S. Cl. ............ 424/401; 252/309; 252/312; 424/59; 424/60; 424/400; 514/938; 514/944
[58] Field of Search ............... 424/59, 60, 400, 424/401; 252/309, 312; 514/938, 944

[56] References Cited

U.S. PATENT DOCUMENTS 5,332,595  7/1994  Gaonkar .................... 426/602

FOREIGN PATENT DOCUMENTS 2162821  5/1996  Canada .
95/31967  11/1995  WIPO .
98/24399  6/1998  WIPO .

OTHER PUBLICATIONS

Fox, "An Introduction to Multiple Emulsions" *Cosmetics and Toiletry,* vol. 101, Nov., 1986, pp. 101–112.

*Primary Examiner*—Shelley A. Dodson
*Attorney, Agent, or Firm*—Rimma Mitelman

[57] ABSTRACT

The inventive compositions contain an oil-in-water and a water-in-oil emulsion, each buffered to a specific pH, so that the difference in pH values of the two emulsions is at least two units. The molecular mixing is minimized by selecting suitable oil and oil phase in a water-in-oil emulsion. The change in pH is further minimized by buffering each emulsion. The particular advantage of the inventive compositions is the ability to separate within a single composition, with minimal intermixing, active compounds which require different pH environments for stability and/or optimum efficacy.

7 Claims, No Drawings

STABLE COSMETIC COMPOSITIONS WITH DIFFERENT PH EMULSIONS

FIELD OF THE INVENTION

The invention relates to cosmetic compositions for skin which contain at least two emulsions in interfacial contact with each other, each of the emulsions having a different, stably maintained pH environment.

BACKGROUND OF THE INVENTION

Cosmetic products which improve the appearance of skin are increasingly popular with consumers. Frequently, consumers seek to alleviate or delay the signs of aged or photoaged skin, such as fine lines and wrinkles, dry and sagging skin. At the same time, consumers may also seek other benefits in addition to anti-aging, which requires the manufacturer to incorporate several active ingredients into a cosmetic product. Also, cosmetic industry manufacturers continuously strive to improve the efficacy of anti-aging products by combining several anti-aging ingredients.

Unfortunately, it is often difficult to combine various active ingredients, while maintaining their optimum stability. For instance, optimum stability of ascorbic acid is at an acidic pH, yet retinol is particularly unstable at an acidic pH, even though it may be stabilized at a neutral pH. Thus, a product containing ascorbic acid and retinol must keep the actives at two different pH values. While other carboxylic acids, including hydroxy acids, might not have the same stability problem, the acid exists in a formulation only at a lower pH; salts are formed at a higher pH, yet the hydroxy acids are most effective at an acidic pH. Again, the need exists to maintain hydroxy acids and retinol at two different pHs. Currently, the incompatible actives (i.e., actives which require different pH environments for stability or chemical activity) are protected by separating them in double barrel chambers. Another conceivable separation method is to sequester the actives in different phases of a multiple emulsion (e.g., oil-in-water-in-oil or water-in-oil-in-water). Double barrel chambers, however, are too costly for mass market applications and multiple emulsions are known to be very fragile (see Fox, Cosmetics and Toiletry, vol. 101, November 1986, p 101–112).

Canadian Patent Application 2,162,821 (Colgate-Palmolive) discloses a multilayer bicarbonate/peroxide dentifrice. Bicarbonate and peroxide are maintained in stable discrete layers. The composition of the two layers is very different from the cosmetic emulsions employed in the present invention. Indeed, in the '821 application the two layers are essentially anhydrous systems. Furthermore, the '821 application does not mention any pH values and does not employ emulsions with different pH values.

SUMMARY OF THE INVENTION

Many cosmetic products are creams and ointments which are resistant to macroscopic (i.e., gross) mixing with each other. Such emulsions may still permit microscopic molecular mixing by diffusion. The inventive compositions contain an oil-in-water and a water-in-oil emulsion, each buffered to a specific pH, so that the difference in pH values of the two emulsions is at least two units. The molecular mixing is minimized in the present invention by selecting the oil in the oil phase in a water-in-oil emulsion of certain solvency properties. In addition, the oil phase in a water-in-oil emulsion must have viscosity in a specific range. The change in pH is further minimized by buffering each emulsion.

The stability problem inherent to multiple emulsions is prevented in the inventive compositions by having two separate emulsions instead of a single multiple emulsion. Similarly, the need for costly double barrel packaging is avoided by using the emulsions' physical properties as the barrier to mixing. The particular advantage of the inventive compositions is the ability to separate within a single composition, with minimal intermixing, active compounds which require different pH environments for stability and/or optimum efficacy.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the individual emulsions, unless otherwise specified.

The inventive cosmetic compositions for application to skin comprise at least two emulsions in an interfacial contact with each other. One of the emulsions is a water-in-oil emulsion which is included in the composition in an amount of from 10 to 60%, preferably 25 to 60%, most preferably 40 to 60% by weight of the composition. A second emulsion is an oil-in-water emulsion which is included in the composition in a amount of from 40 to 90%, preferably from 40 to 75%, most preferably from 40 to 60% by weight of the composition. Oil-in-water emulsion preferably is present in a greater amount since it is more aesthetically preferred. The water-in-oil and the oil-in-water emulsion each contains an aqueous and an oil phase in the amounts specified in the table below:

| Phase | Wt. % Range | | |
| --- | --- | --- | --- |
| | General | Preferred | Most Preferred |
| Water-in-oil emulsion | | | |
| aqueous phase | 30–80 | 40–80 | 60–80 |
| oil phase | 20–70 | 20–60 | 20–40 |
| Oil-in-water emulsion | | | |
| aqueous phase | 40–99 | 50–95 | 70–85 |
| oil phase | 1–60 | 5–50 | 15–30 |

The yield stress of each of the emulsions is in the range of from 10 Pa to 1,000 Pa, preferably 10 to 500 Pa, most preferably 20 to 300 Pa to minimize macroscopic mixing while also optimizing the aesthetics of the inventive product and the ease of use.

The oil phase of the water-in-oil emulsion is selected according to the present invention to have specific viscosity. The viscosity is generally in the range of from 100 to 100,000 mPa.sec. The viscosity of the oil phase must be high enough to prevent microscopic mixing, yet not too high to prevent the emulsion from being too thick to use.

The oil in the oil phase of the water-in-oil emulsion is selected according to the present invention to have a specific solvency. The solvency of the oil is characterized by the distribution coefficient ($K_S$) of fully protonated lactic acid between the oil and water. ('Lactic Acid; Properties and Chemistry of Lactic Acid and Derivatives', by C. H. Holten; p39, Verlag Chemie 1971).

The proper selection of $K_S$ is important so as to minimize the solubility of water and water soluble active in the oil.

According to the present invention, $K_S$ is between 0 and 0.2, preferably from 0 to 0.1 and most preferably between 0 and 0.05.

Suitable oils for the oil phase of a water-in-oil emulsion selected from the group consisting of aliphatic hydrocarbons (e.g., mineral oils), aromatic hydrocarbons (e.g., Limonene), esters of fatty acids and alcohol (e.g., amyl acetate). These oils are suitable as long as they satisfy the $K_S$ requirement specified above.

According to the present invention, the pH values of the water-in-oil and oil-in-water emulsions differ by at least two pH units. The different pH environments of the two emulsions can be stably maintained within a single inventive composition by virtue of employing emulsions of specific viscosity, selection of specific oil and oil phase for the water-in-oil emulsion and incorporating a buffer into an aqueous phase of each emulsion. Whenever the pH value of the water-in-oil emulsion is discussed herein, the pH referred to is actually the pH of the water phase of the water-in-oil emulsion.

The buffers are made from mixtures of weak carboxylic acids and their corresponding salts, or weak bases and their corresponding salts. Examples of suitable carboxylic acids include but are not limited to: alpha- or beta-hydroxy acids, dicarboxylic acids, tricarboxylic acids, ascorbic acid, oxamic acid and mixtures thereof. Examples of suitable weak bases include but are not limited to: glycine derivatives, tris(hydroxymethyl) amino methane, triethanol amine, tetraacetyl phytosphingosine and phosphates. Preferred carboxylic acids are glycolic acid, lactic acid, malic acid, beta-hydroxybuturic acid, acetic acid, succinic acid, citric acid, ascorbic acid, oxamic acid, and mixtures thereof. Preferred bases are phosphates and triethanolamine.

The exact identity and the amounts of these acids and bases for making up a buffer are selected according to the desired pH. The buffers are chosen so that their respective pKa value is close to the desired pH of value of the respective buffers (usually, pKa within +/−1 pH unit). The best buffer is made when the pKa of an acid or base is equal to the pH of the buffer.

Preferably, when an acidic pH is required (i.e., pH 3 to 5) the buffer is made of the combination selected from the group consisting of glycolic acid and its salt, lactic acid and its salt, citric acid and its salt, acetic acid and its salt, or succinic acid and its salt. When a neutral pH buffer is required (i.e., pH 6 to 8), the buffer is preferably made of phosphate monobasic and phosphate dibasic. When a basic pH is required (i.e., pH 8 to 10) the buffer is preferably made of carbonate and bicarbonate.

The relative concentrations of two buffers with regard to each other depend on the pH that is desired to result from the mixing of two emulsions at the point of or right after application to the skin ("in use pH"). Thus, in use pH determines the pH value of the stronger buffer which should be preferentially within +/−1 pH unit of the in use pH. The pH value of the weaker buffer depends on the pH at which the molecule that is desired to be stabilized has the best stability. The molality of one of the two buffers is chosen either arbitrarily or based on the concentration of an active ingredient in the desired final composition (e.g., when the active ingredient is also a suitable weak acid for making a buffer such as a hydroxy acid or ascorbic acid or another carboxylic acid.) The molality of the other buffer is determined by performing a titration test.

The inventive compositions are particularly useful when it is desired to separate two active ingredients which need different pH environments for storage stability and/or optimum efficacy. Thus, in a preferred embodiment of the invention the composition incorporates carboxylic acids in one half of the product and a retinoid in the other half of the product.

Examples of suitable carboxylic acids are the same acids as those listed for making an acidic buffer above. Most preferred composition according to the present invention contain an acid selected from the group consisting of glycolic, lactic, succinic, oxamic or ascorbic acid in one half of the product at an acidic pH and retinol or short chain esters thereof in the other half of the product at a neutral pH. A carboxylic acid can also serve as a suitable buffer. In such instances, it must be calculated whether the amount needed for the activity of a carboxylic acid to deliver cosmetic benefit is sufficient to maintain buffering capacity. If not so, the buffer must be supplemented with another acid. Preferably the amount of the carboxylic acid component present in the composition for efficacy according to the invention is from 0.01 to 20%, more preferably from 0.05 to 12% and most preferably from 0.5 to 8%, by weight of the composition.

The term "retinoid" as used herein means "retinol" or $C_2$–$C_5$ retinyl ester thereof. The term "retinol" as used herein includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Most preferred is all-trans-retinol, due to its wide commercial availability.

Retinyl ester is an ester of retinol. Retinyl esters suitable for use in the present invention are $C_2$–$C_5$ esters. Preferably, $C_2$ and $C_3$ esters of retinol, also known as retinyl acetate and retinyl propionate are employed. Retinyl acetate is an especially preferred ester because it is the most efficacious, the most commercially available and the cheapest. For the same reasons, the most preferred retinoid for use in the present invention is retinol.

Retinol or a retinyl ester is employed in the inventive composition in an amount of from 0.001% to 10%, preferably in an amount of from 0.01% to 0.5%, most preferably in an amount of from 0.05% to 0.2%, by weight of the composition.

Hydroxy acids are more effective when applied at a relatively acidic pH, i.e., pH=3–5. Ascorbic acid is more stable at an acidic pH, i.e. pH=2–4. On the other hand, retinoids, especially retinol and/or short chain esters thereof, i.e., $C_2$–$C_5$ esters of retinol are more stable at a neutral pH, i.e. pH=6–8.

The inventive compositions containing carboxylic acids and retinoids may be employed to reduce appearance of wrinkles, aged or photoaged skin, improve skin color, improve skin's radiance and clarity and/or impart overall healthy and youthful appearance of the skin.

Preferably, a surfactant employed in making the water-in-oil emulsion is a polymeric surfactant, so that it does not transport water or water soluble active across the oil phase of the water-in-oil emulsion. Suitable polymeric surfactants include but are not limited to: polyacrylamides e.g., Sepigel 305™ which is a mixture of polyacrylamide, isoparaffin, and laureth 7), silicone copolyols, specifically cetyl dimethicone copolyol, (e.g., Trade name: Abil EM-90 supplied from Goldschmidt), pegylated polyhydroxyalkyls such as PEG-30 dipolyhydroxystearate(Trade name: Arlacel P135 supplied from ICI). The polymeric surfactant is employed generally in an amount from 0.5 to 10 wt. %, preferably in an amount from 1.0 to 5.0 wt. % of water-in-oil emulsion.

Optional Skin Benefit Materials and Cosmetic Adjuncts

The oil phase of the water-in-oil emulsion acts as a barrier between the oil-in-water emulsion and the aqueous phase of the water-in-oil emulsion. Thus, the water-in-oil emulsion should not include any ingredients in quantities that will alter the viscosity of the oil phase and the oil-in-water distribution coefficient of the oil in the oil phase to a degree where it is no longer suitable for use in the present invention. Consequently, optional ingredients are preferably incorporated into the oil-in-water emulsion.

The aqueous phase of the oil-in-water emulsion can include, in addition to water, a co-solvent, humectants, thickeners and powders. An especially preferred co-solvent is a polydimethyl siloxane and/or a polydimethyl phenyl siloxane. Silicones of this invention may be those with viscosities ranging anywhere from about 10 to 10,000,000 $m^2/s$(centistokes) at 25° C. Especially desirable are mixtures of low and high viscosity silicones. These silicones are available from the General Electric Company under trademarks Vicasil, SE and SF and from the Dow Corning Company under the 200 and 550 Series. Amounts of silicone which can be utilized in the compositions of this invention range anywhere from 5% to 60%, preferably from 25% to 60% by weight of the composition.

The inventive compositions may include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

Use of the Composition

The composition according to the invention is intended primarily as a product for topical application to human skin, especially as an agent for conditioning, moisturizing and smoothening the skin, increasing its thickness, flexibility and elasticity and preventing or reducing the appearance of wrinkled, lined or aged skin.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device. Preferably, the two emulsions are mixed on the skin together by rubbing.

Product Packaging

The inventive skin cosmetic composition can be packaged in a suitable container to suit its viscosity and intended use by the consumer. Or the composition can simply be stored in a non-deformable bottle or squeeze container, such as a tube or a lidded jar. The composition may also be included in capsules such as those described in U.S. Pat. No. 5,063,057, incorporated by reference herein. The invention accordingly also provides a closed container containing a cosmetically acceptable composition as herein defined.

The following specific examples further illustrate the invention, but the invention is not limited thereto.

EXAMPLES

Oil-in-Water Emulsion Base

This formulation (O/W Base 1) was the base for all oil-in-water emulsions used in the Examples.

| FULL CHEMICAL NAME OR CTFA NAME | WT % | TRADE NAME AND % ACTIVE AS RECEIVED | PHASE |
|---|---|---|---|
| disodium EDTA | 0.05 | Sequesterene Na2 | water |
| magnesium aluminum silicate | 0.6 | Veegum Ultra | water |
| methyl paraben | 0.15 | Methyl Paraben | water |
| simethicone | 0.01 | DC Antifoam Emulsion | water |
| butylene glycol 1,3 | 3.0 | Butylene Glycol 1,3 | water |
| hydroxyethylcellulose | 0.5 | Natrosol 250HHR | water |
| glycerine, USP | 2.0 | Glycerine USP | water |
| xanthan gum | 0.2 | Keltrol 1000 | water |
| triethanolamine | 1.2 | Triethanolamine 99% | water |
| stearic acid | 3.0 | Pristerene 4911 | oil |
| propyl paraben NF | 0.1 | Propylparaben NF | oil |
| glyceryl hydrostearate | 1.5 | Naturechem GMHS | oil |
| stearyl alcohol | 1.5 | Lanette 18DEO | oil |
| isostearyl palmitate | 6.0 | Protachem ISP | oil |
| C12–15 alcohols octanoate | 3.0 | Hetester FAO | oil |
| dimethicone | 1.0 | Silicone Fluid 200 (50 cts) | oil |
| cholesterol NF | 0.5 | Cholesterol NF | oil |
| sorbitan stearate | 1.0 | Sorbitan Stearate | oil |
| butylated hydroxytoluene | 0.05 | Embanox BHT | oil |
| tocopheryl acetate | 0.1 | Vitamine E Acetate | oil |
| PEG-100 stearate | 2.0 | MYRJ 59 | oil |
| sodium stearoyl lactylate | 0.5 | Pationic SSL | oil |
| hydroxycaprylic acid | 0.1 | Hydroxycaprylic Acid | water |
| water, DI | q.s. to 75% | | water |

Water in Oil Base

This formulation (W/O Base 1) was the base for all water in oil emulsions used in the Examples, except in Example 5.

| FULL CHEMICAL NAME | WT % | TRADE NAME | PHASE |
|---|---|---|---|
| Cetyl Dimethicone Copolyol | 3.0 | Abil EM 90 | Oil |
| Mineral Oil | 17.0 | Carnation Light Mineral Oil | Oil |
| Microcrystalline Wax | 10.0 | Multiwax W835 | Oil |

The oil/water distribution coefficient ($K_S$) of the oil was determined as follows:

A 0.05% (5.6 mM) aqueous solution of radiolabeled ($^{14}C$) lactic acid solution was prepared in 3.3 mM aqueous sulfuric acid solution (pH 2.4) previously saturated with Carnation Light mineral oil. Radiolabeled lactic acid was used for accurate measurements of low level of lactic acid in the oil. The low pH of the water phase was maintained to ensure that lactic acid was completely protonated. Triplicate aliquots of this aqueous phase were equilibrated with equal volumes of Carnation Light mineral oil previously saturated with 3.3 mM aqueous $H_2SO_4$. Equilibrium between the oil and water phases was attained by gently inverting the tubes 100 times in approximately 5 minutes. The mixtures were centrifuged and aliquots of each phase sonicated in 5 volumes of water to disperse/extract lactic acid from the oil phase. The dispersed samples were counted by liquid scintillation spectrometry (using Beckman LS65 Scintillation counter) and $K_S$ was calculated as the radioactive counts in the oil phase divided by the counts in the aqueous phase.

The $K_S$ of lactic acid in mineral oil water system was determined to be 0.0004.

Oil phase viscosity of the water-in-oil emulsion is determined as follows:

Viscosity was determined at a temperature of 50° C. using a Carri Med CSL controlled stress rheometer. A parallel plate geometry was used of the following dimensions: 4 cm diameter, stainless steel, serrated face, gap set at 100 micron. The sample was loaded into the rheometer, and ramped using a torque sweep. The sample was ramped from a torque value of 0 micro Nm to 500 micro Nm over a time period of 5 minutes. Upon completion of the ramp, the viscosity is measured at a shear rate of 1 reciprocal second.

The viscosity of the oil phase of W/O Base 1 was determined by the oil phase viscosity test and found to be 5,000 mPa.s.

Yield stress of both emulsions was determined as follows:

Equipment: Carri Med CSL100 Rheometer

Parallel plate geometry, 4 cm diameter, stainless steel, serrated face; gap size 100 micron Temperature 25° C.

Samples were ramped by varying the applied torque from a value of 0 to 1000 micro N.m over a time period of 5 minutes. This range is appropriate for low viscosity lotions. For more viscous creams, a larger range is needed and the sample which procedure was used is ramped from 0 to 3500 micro N.m over a time range of 5 minutes. Beginning from an applied torque of 0 micro N.m, a specific torque must be reached before the rheometer registers flow, and this torque depends on the viscosity of the product. This minimum torque when flow begins is the yield torque. To convert the yield torque to a yield stress, the following equation was used for a parallel plate geometry:

$$stress = 2(torque)/3.142\, BR^3$$ where R is the radius of the plate.

To obtain a stress value in units of Pa, torque must be in units of N.m, and radius of plate in units of m.

The yield stress that was determined for each emulsion is given in the tables below.

Both the negative controls and the test samples in the Examples below were prepared as follows:

Wide mouth nalgene plastic jars were separated into two halves with a piece of cardboard. The emulsion containing an alpha-hydroxy acid or ascorbic acid was added to one half of the jar. The viscosity of these emulsions, even in the negative controls, was high enough so that they retain their shape and do not flow to the other side. The jar was then placed in a freezer (−6° C.) for about twenty minutes, until the emulsion hardened enough so that it held its shape when the cardboard barrier was removed. The second emulsion was then added to the empty half of the jar.

All emulsions in the examples were buffered with acids/bases, as indicated in the tables. The amounts of acids/bases to buffer the emulsion were calculated using a titration test, as known to a chemist of ordinary skill.

Criteria for the Titration Test 1. strong buffer can accommodate as much as 20% w/w of weak buffer with its pH changing by no more than one pH unit;
2. when water-in-oil emulsion and oil-in-water emulsion are mixed, the resulting pH is equal to desired in-use pH (close to strong buffer pH).

Example 1

The pH stability of the compositions containing two emulsions (one at pH 4 and the second at pH 7) was investigated.

Negative Control (composition outside the scope of the invention) consisted of two oil-in-water emulsions: A1 and B1. Each emulsion consisted of 80% aqueous phase and 20% oil phase. The negative control composition contained A1 and B1 (details of formulations in Table 1) in a ratio 1:1 side by side in a single compartment jar.

Test Sample (within the scope of the invention) consisted of a water-in-oil emulsion (Formulation C1) and an oil-in-water emulsion (Formulation D1). Formulation C1 contained 70% by weight aqueous phase and 30% oil phase. Formulation D1 contained 80% aqueous phase and 20% oil phase. The test sample contained a 1:1 ratio of C1 and D1 (details of formulations in Table 1) side by side in a single compartment jar. At the point of application to skin, when the emulsions C1 and D1 were mixed in a 1:1 ratio, a pH 4 emulsion resulted.

In this Example, a mixture of Sodium Phosphate Mono and Dibasic is a weak buffer, Glycolic Acid and its salt is a strong buffer.

Formulations A1, B1, C1 and D1 are summarized in Table 1 below:

TABLE 1

| Name | Emulsion Type | pH | Ingredients | % W/W | Yield Stress (Pa) |
|---|---|---|---|---|---|
| A1 | O/W | 4 | O/W Base 1 | 75 | 103 |
|  |  |  | 70% Glycolic Acid | 11.43 |  |
|  |  |  | 29% Ammonium Hydroxide | 2.5 |  |
|  |  |  | Water | q.s. 100% |  |
| B1 | O/W | 7 | O/W Base 1 | 75 | 90 |
|  |  |  | Sodium Phosphate Monobasic | 1.1 |  |
|  |  |  | Sodium Phosphate Dibasic | 3.3 |  |
|  |  |  | Water | q.s. 100% |  |
| C1 | W/O | 4 | W/O Base 1 | 30 | 46 |
|  |  |  | 88% Lactic Acid | 9.1 |  |
|  |  |  | 29% Ammonium Hydroxide | 2.6 |  |
|  |  |  | Water | q.s. 100% |  |
| D1 | O/W | 7 | Same as B1 | Same as B1 | 90 |

*O/W = oil-in-water
**W/O = water-in-oil pH change on the pH 7 side of the dual jars containing the negative control and the test sample was monitored. The results that were obtained are summarized in Table 2.

TABLE 2

| Day | Test Sample pH | Negative Control pH |
|---|---|---|
| 0 | 7.3 | 7.0 |
| 3 | 7.3 | — |
| 5 | — | 6.8 |
| 7 | 7.3 | — |
| 13 | 7.3 | — |
| 19 | 7.3 | 4.6 |
| 27 | 7.2 | — |
| 29 | — | 4.3 |
| 35 | — | 4.2 |
| 41 | 7.3 | — |
| 49 | — | 4.4 |

Example 2

The pH stability of the compositions containing two emulsions (one at pH 4 and the second at pH 6) was investigated.

Negative Control (composition outside the scope of the invention) consisted of two oil-in-water emulsions: A1 and B1. Each emulsion consisted of 80% aqueous phase and 20% oil phase. The negative control composition contained A1 and B1 (details of formulations in Table 3) in a ratio 1:1 side by side in a single compartment jar.

Test Sample (within the scope of the invention) consisted of two emulsions: a water-in-oil emulsion (Formulation C2) and an oil-in-water emulsion (Formulation D2). Formulation C2 contained 70% by weight aqueous phase and 30% oil phase. Formulation D2 contained 80% aqueous phase and 20% oil phase. The test sample contained a 1:1 ratio of C1 and D1 (details of formulations in Table 3) side by side in a single compartment jar. At the point of application to skin, when the emulsions C2 and D2 were mixed in a 1:1 ratio, a pH 4 emulsion resulted.

In this Example, a mixture of Sodium Phosphate Mono and Dibasic is a weak buffer, Glycolic Acid and its salt is a strong buffer.

TABLE 3

| NAME | Emulsion Type | pH | Ingredients | % W/W | Yield Stress (Pa) |
|---|---|---|---|---|---|
| A2 | O/W | 4 | O/W Base 1 | 75 | 103 |
|  |  |  | 70% Glycolic Acid | 11.43 |  |
|  |  |  | 29% Ammonium Hydroxide | 2.5 |  |
|  |  |  | Water | q.s. 100% |  |
| B2 | O/W | 6 | O/W Base 1 | 75 | 90 |
|  |  |  | Sodium Phosphate Monobasic | 2.44 |  |
|  |  |  | Sodium Phosphate Dibasic | 0.66 |  |
|  |  |  | Water | q.s. 100% |  |
| C2 | W/O | 4 | W/O Base 1 | 30 | 46 |
|  |  |  | 88% Lactic Acid | 9.1 |  |
|  |  |  | 29% Ammonium Hydroxide | 2.6 |  |
|  |  |  | Water | q.s. 100% |  |
| D2 | O/W | 6 | Same as B2 | Same as B2 | 90 | pH change on the pH 6 side of the dual jars containing the negative control and the test sample was monitored. The results that were obtained are summarized in Table 4.

TABLE 4

| Day | Test Sample pH | Negative Control pH |
| --- | --- | --- |
| 0 | 6.05 | 6.05 |
| 1 | 6.07 | 6.06 |
| 3 | 6.15 | 5.20 |
| 7 | 6.11 | 4.92 |
| 11 | 6.10 | 4.48 |
| 17 | 6.14 | 4.28 |
| 37 | 5.96 | 4.00 |

Example 3

The pH stability of the compositions containing two emulsions (one at pH 4 and the second at pH 10) was investigated.

Negative Control (composition outside the scope of the invention) consisted of two oil-in-water emulsions: A3 and B3. Each emulsion consisted of 80% aqueous phase and 20% oil phase. The negative control composition contained A3 and B3 (details of formulations in Table 3) in a ratio 1:1, side by side in a single compartment jar.

Test Samples (within the scope of the invention) consisted of two emulsions: a water-in-oil emulsion (Formulation C3) and an oil-in-water emulsion (Formulation D3). Formulation C3 contained 70% by weight aqueous phase and 30% oil phase. Formulation D3 contained 80% aqueous phase and 20% oil phase. The test sample contained a 1:1 ratio of C3 and D3 (details of formulations in Table 5) side by side in a single compartment jar. At the point of application to skin, when the emulsions C3 and D3 were mixed in a 1:1 ratio, a pH 4 emulsion resulted.

TABLE 5

| NAME | Emulsion Type | pH | Ingredients | % W/W | Yield Stress (Pa) |
| --- | --- | --- | --- | --- | --- |
| A3 | O/W | 4 | O/W Base 1 | 75 | 103 |
| | | | 70% Glycolic Acid | 11.43 | |
| | | | 29% Ammonium Hydroxide | 2.5 | |
| | | | Water | q.s. 100% | |
| B3 | O/W | 10 | O/W Base 1 | 75 | 219 |
| | | | Sodium Bicarbonate | 0.8 | |
| | | | Sodium Carbonate | 4.3 | |
| | | | Water | q.s. 100% | |
| C3 | W/O | 4 | W/O Base 1 | 30 | 46 |
| | | | 88% Lactic Acid | 9.1 | |
| | | | 29% Ammonium Hydroxide | 2.6 | |
| | | | Water | q.s. 100% | |
| D3 | O/W | 10 | Same as B3 | Same as B3 | 219 | pH change on the pH 10 side of the dual jars containing the negative control and the test sample was monitored. The results that were obtained are summarized in Table 6.

TABLE 6

| Day | Test Sample pH | Negative Control pH |
| --- | --- | --- |
| 0 | 9.75 | 9.75 |
| 2 | 9.72 | 8.62 |
| 6 | 9.75 | 8.3 |
| 10 | 9.67 | 7.93 |
| 16 | 9.66 | 7.80 |
| 36 | 9.63 | 7.46 |

Example 4

The pH stability of the compositions containing two emulsions (one at pH 7 and the second at pH 10) was investigated.

Negative Control (composition outside the scope of the invention) consisted of two oil-in-water emulsions: A4 and B4. Each emulsion consisted of 80% aqueous phase and 20% oil phase. The negative control composition contained A4 and B4 (details of formulations in Table 3) in a ratio 1:1 side by side in a single compartment jar.

Test Sample (within the scope of the invention) consisted of two emulsions: a water-in-oil emulsion (Formulation C4) and an oil-in-water emulsion (Formulation D4). Formulation C4 contained 70% by weight aqueous phase and 30% oil phase. Formulation D4 contained 80% aqueous phase and 20% oil phase. The test sample contained a 1:1 ratio of C4 and D4 (details of formulations in Table 7) side by side in a single compartment jar. At the point of application to skin, when the emulsions C4 and D4 were mixed in a 1:1 ratio, a pH 7 emulsion resulted.

In this Example, Sodium Phosphate Mono and Dibasic is the strong buffer and carbonate/bicarbonate is the weak buffer.

TABLE 7

| NAME | Emulsion Type | pH | Ingredients | % W/W | Yield Stress (Pa) |
| --- | --- | --- | --- | --- | --- |
| A4 | O/W | 10 | O/W Base 1 | 75 | 219 |
| | | | Sodium Bicarbonate | 0.8 | |
| | | | Sodium Carbonate | 4.3 | |
| | | | Water | q.s. 100% | |
| B4 | O/W | 7 | O/W Base 1 | 75 | 90 |
| | | | Sodium Phosphate Monobasic | 1.1 | |
| | | | Sodium Phosphate Dibasic | 3.3 | |
| | | | Water | q.s. 100% | |
| C4 | W/O | 7 | Same as B4 | Same as B4 | 90 |
| D4 | W/W | 10 | Same as A4 | Same as A4 | 219 | pH change on the pH 10 side of the dual jars containing the negative control and the test sample was monitored. The results that were obtained are summarized in Table 8.

TABLE 8

| Day | Test Sample pH | Negative Control pH |
| --- | --- | --- |
| 0 | 9.75 | 9.75 |
| 2 | 9.72 | 9.66 |
| 6 | 9.73 | 9.55 |
| 10 | 9.67 | 9.37 |
| 16 | 9.69 | 9.28 |
| 36 | 9.68 | 9.08 |

The results in Tables 2, 4, 6 and 8 demonstrate that molecular diffusion was effectively controlled in the test samples, but not in the negative controls where the diffusion was evident: the pH of the test samples was substantially constant, and the pH of the negative controls dropped dramatically. Thus, the presence of the water-in-oil emulsion according to the invention is necessary to maintain effective pH separation (pH 4 vs. pH 7 in Example 1; pH 4 vs. pH 6 in Example 2; pH 4 vs. pH 10 in Example 3; and pH 7 vs. pH 10 in Example 4).

Example 5

The stability of ascorbic acid was compared in an oil-in-water emulsion at pH 7 to the stability in the inventive composition according to the invention, wherein the ascorbic acid was solubilized in the aqueous phase of a water-in-oil emulsion at pH 3 with an oil-in-water emulsion co-present in the composition.

Negative Control (Formulation A5; details in Table 9) contained 80% aqueous phase and 20% oil phase by weight.

Test Sample contained ascorbic acid in water-in-oil emulsion at pH 3 (Formulation C5) with oil in water emulsion at pH 7 (Formulation D5) side by side, in a 1:1 ratio, in a single jar. Formulation C5 contained 33% aqueous phase and 67% oil phase by weight. Formulation D5 contained 80% aqueous phase and 20% oil phase by weight When both emulsions in the composition were mixed in equal volumes at the point of application to skin, a pH 7 product resulted. In this experiment, sodium phosphate monobasic and dibasic is the strong buffer, and ascorbic acid and citric acid and their salts is the weak buffer.

TABLE 9

| NAME | Emulsion Type | pH | Ingredients | % W/W | Yield Stress (Pa) |
|---|---|---|---|---|---|
| A5 | O/W | 7 | O/W Base 1 | 75 | 100 |
|  |  |  | Ascorbic Acid* | 2.5 |  |
|  |  |  | Sodium Phosphate Monobasic | 1.1 |  |
|  |  |  | Sodium Phosphate Dibasic | 3.3 |  |
|  |  |  | Water | q.s. 100% |  |
| C5 | W/O | 3 | see Table 9A below | see Table 9A below | 50 |
| D5 | O/W | 7 | O/W Base 1 | 75 | 90 |
|  |  |  | Sodium Phosphate Monobasic | 1.1 |  |
|  |  |  | Sodium Phosphate Dibasic | 3.3 |  |
|  |  |  | Water | q.s. 100% |  |

*from J. T. Baker Chemical Co.

TABLE 9A

| FULL CHEMICAL NAME OR CTFA NAME | % ACTIVE LEVEL IN FORMULATION | TRADE NAME AND % ACTIVE AS RECEIVED | Phase |
|---|---|---|---|
| Water, DI | 30.0 | Water, DI | Water |
| Cetyl Dimethicone Copolyol | 3.0 | Abil EM 90 | Oil |
| Mineral Oil | 43.8 | Carnation Light Mineral Oil | Oil |
| Microcrystalline Wax | 20.0 | Multiwax W835 | Oil |
| Disodium EDTA | 0.05 | Sequesterene Na2 | Water |
| Ascorbic Acid | 2.5 |  | Water |
| Sodium Phosphate Dibasic | 0.273 |  | Water |
| Citric Acid | 0.382 |  | Water |

Ascorbic Acid Stability Data (expressed as percent Ascorbic Acid in Formulation) was measured in the negative control and in the test sample.

HPLC Method to Determine Ascorbic Acid Concentration:

Column: Anion Exclusion (Alltech, P/N 269006)

Mobil Phase: 10 mM $H_2SO_4$

Flow Rate: 1.0 mL/min

Detection: UV, 254 nm

Injection Vol.: 10 microliters

Prepare the ascorbic acid stock solution (approximately 1000 ppm) by dissolving it in absolute ethanol. Prepare four standard solutions (5–15 ppm) by diluting each aliquot in 70/30 ethanol/water. Filter each solution using 0.45 micron disposable filter prior to injection. From the chromatogram, obtain the area response corresponding to each standard solution and plot the standard curve using RS4 or equivalent.

Prepare the sample (100–300 ppm) by dissolving it in 70/30 ethanol/water. Sonicate sample is completely dissolved. Filter the sample solution using 0.45 micron disposable filter prior to injection. Sample solutions should be analyzed immediately to minimize ascorbic acid breakdown.

The level of ascorbic acid in the sample can be calculated from the standard curve.

The results that were obtained are summarized in Table 10.

TABLE 10

| Day | Test Sample | Negative Control |
|---|---|---|
| 0 | 2.5 | 1.8 |
| 7 | 2.2 | 1.3 |
| 12 | 2.1 | 1.0 |
| 18 | 1.9 | 0.9 |

It can be seen from the results in Table 10, that although both samples were formulated with 2.5% ascorbic acid, the initial analysis (day 0) for the negative control showed the presence of only 1.8% ascorbic acid, indicating that a degradation of ascorbic acid had occurred during the time it took to formulate the product. Ascorbic acid continued to degrade substantially more rapidly in the negative control compared to the test sample. The results in Table 10 demonstrate the criticality of the presence of the two emulsions according to the invention to stabilize ascorbic acid.

Example 6

The stability of retinol in an oil-in-water emulsion also containing a hydroxy acid (emulsion pH=3.6) was compared to the stability of retinol in an oil-in-water emulsion at pH 7.0 and also to the stability of retinol in an oil-in-water emulsion at pH 7.0, when co-present with water-in-oil emulsion at pH 3.6 containing a hydroxy acid.

Negative Control: Oil in water emulsion A6 containing 0.15% Retinol at pH 3.6 (8% glycolic acid); details of formulation given in Table 11.

Positive Control: Oil in Water Emulsion B6 containing 0.15% Retinol at pH 7.0; details of formulation given in Table 11.

Test sample contained Oil in Water Emulsion containing 0.15% Retinol at pH 7.0 (C6) side by side with an water-in-oil emulsion containing 8% lactic acid pH 3.6 (D6) in a 1:1 ratio. When equal amounts by weight of the two emulsions were mixed (as would occur during application of the product), the final pH of the emulsion was 3.8.

TABLE 11

| NAME | Emulsion Type | pH | Ingredients | % W/W | Yield Stress (Pa) |
|---|---|---|---|---|---|
| A6 | O/W | 3.6 | O/W Base 1 | 75 | 103 |
|  |  |  | 70% Glycolic Acid | 11.43 |  |
|  |  |  | 29% Ammonium Hydroxide | 2.5 |  |
|  |  |  | Retinol Blend | 0.3 |  |
|  |  |  | Water | q.s. 100% |  |
| B6 | O/W | 7 | O/W Base 1 | 75 | 90 |

TABLE 11-continued

| NAME | Emulsion Type | pH | Ingredients | % W/W | Yield Stress (Pa) |
|---|---|---|---|---|---|
| | | | Sodium Phosphate Monobasic | 1.1 | |
| | | | Sodium Phosphate Dibasic | 3.3 | |
| | | | Retinol Blend* | 0.3 | |
| | | | Water | q.s. 100% | |
| C6 | O/W | 7 | Same as B6 | Same as B6 | 90 |
| D6 | W/O | 3.8 | W/O Base 1 | 30 | 46 |
| | | | 88% Lactic Acid | 9.1 | |
| | | | 29% Ammonium Hydroxide | 2.6 | |
| | | | Water | q.s. 100% | |

*Retinol blend: Retinol 51.3%, BHA 0.6%, BH % (ex. Roche) 3.1%, Tween 45% (Roche).

Retinol stability was measured as a function of time, and half-life calculated for positive control, negative control, and the test sample.

Method of Determining Storage Stability of Retinol:

A composition to be tested was prepared and packaged in a jar. The jar was capped and placed for storage in an oven at 41° C. Our studies have shown that retinol oxidation in compositions evaluated for this invention follows a first order kinetic with respect to retinol concentration. Hence to determine the reaction half-lifetime one would plot the natural logarithm of the retinol concentration (ln C) against the storage time (t) and get a straight line with a slope $-k$ where k is the rate of retinol oxidation in reciprocal unit of time. The half-life of retinol (t1/2) in the system under study is then determined by the ratio ln2/k.

Analysis of Retinol Concentration by HPLC:

All samples were analyzed for retinol content using high pressure liquid chromatography (hardware: Waters 600-MS system controller, Waters 717 autosampler, Waters 996 photodiode array detector, software: Millenium 2010). Column parameters used for retinol analysis are as follows:

| Column: | Nucleosil C18 5 μm (Sigma-Aldrich) 250 mm × 4.6 mm |
|---|---|
| Catalog #: | Z226181 |
| Mobile Phase: | 47% (v/v) Acetonitrile |
| | 45% (v/v) Methanol |
| | 8% (v/v) Methylene Chloride |
| | All HPLC Grade Solvents. |
| Injection volume: | 10 μl |
| Flow Rate: | 1 ml/min |
| Run Time: | 10 minutes |
| Detector: | UV/VISIBLE at 325 nm with Photodiode Array |
| Retention Time: | ca. 5 minutes for retinol. |

Standard Solutions Preparation:

A standard curve was generated whenever samples are analyzed for retinol content. Retinol standard solutions were prepared by diluting serially the retinol blend in isopropanol to yield standard solutions with final concentrations of 0, 10, 20, 30, 40, and 50 ppm (w/w). Standard solutions were prepared on a weekly basis and were stored at $-21°$ C.

Sample Preparation:

In order to ensure the complete extraction of retinol from the emulsion, the sample was treated in the following manner: About 0.5 g of sample, measured precisely, was initially mixed with 6 to 7 grams of water and vortexed to form a slurry. Approximately 10 grams of isopropanol was then added to the slurry followed by a second vortexing period. The sample was then brought to final weight with isopropanol. The sample was subsequently filtered using a disposable syringe fitted with a 0.2 μm disposable filter.

All samples were prepared in triplicate or quintuplicate on a w/w basis using an analytical balance.

The results that were obtained (expressed as % of the initial retinol concentration) are summarized in Table 12.

TABLE 12

| Day | Positive Control | Test Sample | Negative Control |
|---|---|---|---|
| 0 | 100 | 100 | 100 |
| 5 | — | — | 92 |
| 7 | 81 | 91 | — |
| 14 | 67 | 87 | — |
| 19 | 53 | 79 | — |
| 35 | — | — | 67 |
| 45 | — | — | 60 |
| 56 | 30 | 66 | 50 |
| 81 | — | — | 46 |
| 84 | 15 | 60 | — |
| 168 | — | 40 | — |
| Half-life (days) | 168 | 134 | 69 |

It can be seen from the results in Table 12 that retinol was significantly more stable in the inventive formulation (Test Sample) than when stored unprotected in a low pH environment (Negative Control). So the inventive formulation can be used to stabilize retinol (which is sensitive to low pH), even in the co-presence of a low pH environment in the formulation.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A skin cosmetic composition comprising at least two emulsions in an interfacial contact with each other:
    (i) from 10 to 60%, by weight of the composition, of a water-in-oil emulsion, comprising:
        (a) from 30 to 80%, by weight of the water-in-oil emulsion, of an aqueous phase,
        (b) from 20 to 70%, by weight of the water-in-oil emulsion, of an oil phase having a viscosity in the range of from 100 to 100,000 mPa.sec and comprising an oil for which lactic acid oil/water distribution coefficient ($K_s$) is in a range of from 0 to 0.2;
    (ii) from 40 to 90%, by weight of the composition, of an oil-in-water emulsion, comprising:
        (a) from 40 to 99%, by weight of the oil-in-water emulsion, of an aqueous phase,
        (b) from 1 to 60%, by weight of the oil-in-water emulsion, of an oil phase;
    wherein the yield stress of each of the emulsions is in the range of from 10 Pa to 1,000 Pa; and
    wherein each aqueous phase comprises a buffer such that there is a difference of at least two pH units between the water-in-oil emulsion and the oil-in-water emulsion.

2. The composition of claim 1 wherein the pH of the water-in-oil emulsion is in the range of from 3 to 7.

3. The composition of claim 1 wherein the pH of one of the emulsions is an in use pH of the composition and pH of the other emulsion is the pH required for the stability of an ingredient in the other emulsion.

4. The composition of claim 1 wherein the water-in-oil emulsion comprises a polymeric surfactant.

5. The composition of claim 2 wherein the water-in-oil emulsion comprises an alpha-hydroxy acid.

6. The composition of claim 1 wherein the oil-in-water emulsion comprises a retinoid selected from the group consisting of retinol and $C_2$–$C_5$ retinyl esters thereof.

7. The composition of claim 1 wherein the water-in-oil emulsion comprises ascorbic acid.

* * * * *